(12) United States Patent
Abe et al.

(10) Patent No.: US 7,002,041 B2
(45) Date of Patent: Feb. 21, 2006

(54) STABILIZED AMIDE COMPOSITION

(75) Inventors: Takeya Abe, Chiba (JP); Kenju Sasaki, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 188 days.

(21) Appl. No.: 10/286,826

(22) Filed: Nov. 4, 2002

(65) Prior Publication Data

US 2003/0088125 A1    May 8, 2003

(30) Foreign Application Priority Data

Nov. 6, 2001  (JP)  ............................. 2001-340426
Oct. 2, 2002  (JP)  ............................. 2002-290030

(51) Int. Cl.
*C07C 209/90*  (2006.01)

(52) U.S. Cl. .............................. 564/4; 564/1.5; 564/2; 564/204; 564/206; 564/215; 564/216

(58) Field of Classification Search ................. 564/1.5, 564/3, 4, 216, 204, 206, 2
See application file for complete search history.

(56) References Cited

U.S. PATENT DOCUMENTS

| | | | |
|---|---|---|---|
| 3,985,806 A | 10/1976 | Hashimoto et al. | |
| 4,056,565 A | 11/1977 | Matsuda | |
| 4,593,123 A | 6/1986 | Matsuda | |
| 5,352,828 A | 10/1994 | Seki et al. | |
| 5,534,655 A * | 7/1996 | Kambara et al. | ............ 564/127 |

FOREIGN PATENT DOCUMENTS

| JP | B-39-10109 | 3/1960 |
|---|---|---|
| JP | 11-089575 | 4/1999 |

* cited by examiner

*Primary Examiner*—Shailendra Kumar
(74) *Attorney, Agent, or Firm*—Buchanan Ingersoll PC

(57) ABSTRACT

An amide composition containing an unsaturated amide, a sulfur-containing compound, and a weak acid salt. The composition can include an amide in crystalline form or the composition can be in form of aqueous solution. The composition can exhibit improved stability whereby polymerization of the amide is inhibited.

18 Claims, No Drawings

STABILIZED AMIDE COMPOSITION

FIELD OF THE INVENTION

This invention relates to stabilization of an amide such as acrylamide or methacrylamide. An amide such as acrylamide is a useful substance as a starting material for polymers which have many applications such as a coagulating agent, a thickener, a petroleum recovering agent or a paper strength fortifier or a thickening agent for paper-making industries.

BACKGROUND OF THE INVENTION

An amide such as acrylamide is industrially produced by sulfuric-acid hydrolysis method which includes a step of heating a nitrile such as acrylonitrile with sulfuric acid and water to obtain an amidosulfate, a method of hydrating a nitrile in the presence of a catalyst such as copper metal, a copper oxide or a copper salt to obtain a corresponding amide, a method of hydrating a nitrile using a microbial enzyme (nitrile hydratase) to obtain an amide, a method of producing methacrylamide from acetocyanohydrin and so on.

Since an amide is extremely polymerizable, polymerization of an amide can take place in each step of any of the production methods described above or in preservation or deposition of an amide product in a crystalline state or as an aqueous solution. The polymerization can also cause problems such as deterioration in quality, decrease in yield from the production process, obstruction to liquid flow in apparatuses or tubing, and decrease in conduction of heat.

Therefore many kinds of compounds are proposed as a polymerization retarder for an amide. For example, JP-B-39-10109 discloses a method to inhibit polymerization of an amide by adding one or more compounds selected from the group consisting of thiourea, ammonium rhodanide, nitrobenzene, o-tolidine, phenothiazine, and nitroso R salt to the amide so that they coexist with the amide. Further JP-B-2548051 discloses a method for stabilizing an acrylamide solution using water-soluble monocarboxylic acid salts having at least two carbon atoms. (The term "JP-B" as used herein means an "examined Japanese patent publication".)

However, the polymerization inhibition effects of the known methods are not sufficient, and further improvements have been demanded.

SUMMARY OF THE INVENTION

The object of the invention is to provide an amide composition, which is more stable than the amide compositions of conventional techniques.

For example, the invention provides the techniques as shown below.

(1) An amide composition comprising an amide which has an unsaturated bond, a sulfur-containing compound and a weak acid salt.

(2) The amide composition as shown in (1), wherein the sulfur-containing compound is thiourea.

(3) The amide composition as shown in (1), wherein the amide is an unsaturated aliphatic amide.

(4) The amide composition as shown in (1), wherein the amide is acrylamide or methacrylamide.

(5) The amide composition as shown in (1), wherein the sulfur-containing compound is present in an amount in the range of 1 to 100 ppm based on the weight of the amide.

(6) The amide composition as shown in (1), wherein the weak acid salt is a salt of an organic acid, which has an acid dissociation exponent of 3.5 to 5.5.

(7) The amide composition as shown in (1), wherein the weak acid salt is present in an amount in the range of 1 to 3,000 ppm based on the weight of the amide.

(8) The amide composition as shown in (1), wherein the sulfur-containing compound is thiourea, the weak acid salt is a salt of an organic acid having an acid dissociation exponent of 3.5 to 5.5, the thiourea is present in an amount in the range of 1 to 100 ppm based on the weight of the amide and the salt of the organic acid is present in an amount in the range of 1 to 3000 ppm based on the weight of the amide.

(9) The amide composition as shown in any one of (1) to (8), wherein the amide is in a crystalline state.

(10) The amide composition as shown in any one of (1) to (8), wherein the composition is an aqueous solution.

DETAILED DESCRIPTION OF THE INVENTION

Amide

The amide to be used in the invention has an unsaturated bond. An unsaturated amide having 3 to 20 carbon atoms is preferable as the amide to be used in this invention. Among them, an unsaturated aliphatic amide such as acrylamide, methacrylamide or crotonamide is more preferable.

The amide to be used in the invention is typically a monomer. However, the invention can be applied to an amide dimer, an amide trimer, an amide oligomer and so on.

The amide to be used in the invention can be industrially produced by hydrating the corresponding nitrile in the manner of sulfuric-acid hydration method, acetone cyanohydrin method, copper catalyst method, or enzyme method. Among them, the copper catalyst method and enzyme method are most preferable.

The copper method is a method to produce an amide by directly hydrating a nitrile in the presence of copper catalyst such as copper metal, a reduced copper or a Raney copper. Some examples of the method are disclosed in JP-B-52-33092 or JP-B-55-11657.

The enzyme method is a method to produce an amide by hydrating a nitrile by the action of an enzyme (nitrile hydratase) which is obtained by a microorganism and capable of hydrating a nitrile to produce a corresponding amide. A microorganism which contains the enzyme, or a treated substance of the enzyme or the microorganism can also be used instead of the enzyme itself. Some examples of the enzyme method are disclosed in JP-A-11-89575. (The term "JP-A" as used herein means a "unexamined published Japanese patent application".) In the enzyme method, the amount of impurities such as metal ions from a catalyst is small, and the amount of by-products is small since the reaction is conducted at room temperature and atmospheric pressure. Therefore, an amide obtained by the enzyme method has a good stability and a polymerization process of the amide is less affected by the impurities or the by-products. Thus, the enzyme method is especially preferable.

The amide thus produced is available either as an aqueous solution or in a crystalline state by crystallization or drying.

Sulfur-Containing Compound

The sulfur-containing compound to be used in the invention preferably contains at least one nitrogen atom.

The sulfur-containing compound to be used in the invention may be thiourea, phenothiazine and so on. Among them, thiourea is most preferable. The amount of the sulfur containing compound is preferably 1 to 100 ppm, and is more preferably 1 to 30 ppm, based on the weight of the amide respectively.

Weak Acid Salt

The term "weak acid" as used herein means an acid having an acid dissociation exponent measured in water at 25° C. of 2 or more. The acid dissociation exponent of the weak acid is preferably in the range of 2 to 6.5, and more preferably in the range of 3 to 6.

A salt of an organic acid having an acid dissociation exponent measured in water at 25° C. of 3.5 to 5.5 is preferably used as a weak acid salt of the invention. The organic acid may be a saturated aliphatic monocarboxylic-acid, an unsaturated aliphatic monocarboxylic-acid, an aliphatic polycarboxylic-acid, an aromatic carboxylic-acid or the like. Illustrative examples of the saturated aliphatic monocarboxylic-acid include acetic acid, propionic acid, octanoic acid, valeric acid and the like. Illustrative examples of the unsaturated aliphatic monocarboxylic-acid include acrylic acid, crotonic acid, methacrylic acid and the like. Illustrative examples of the aliphatic polycarboxylic-acid include oxalic acid, adipic acid, succinic acid, maleic acid and the like. Illustrative examples of the aromatic carboxylic-acid include benzoic acid and the like. Among these organic acids, acrylic acid and methacrylic acid are most preferable.

The weak acid salt of the invention may be a sodium salt, a potassium salt, an ammonium salt or the like. Among these salts, the sodium salt is most preferable. Sodium acrylate and sodium methacrylate are the most preferable examples of the weak acid salt of the invention.

The weak acid salt can be added to an amide containing solution not only in the form of a salt but also in the form of an acid, provided the weak acid salt is formed in the solution. The amount of the weak acid salt is preferably in the range of 1 to 3,000 ppm based on the weight of the amide. More preferably it is in the range of 1 to 2,000 ppm.

Other Additives

Other additives can be used in the invention as needed. Typical examples of the additives include alkoxy-phenols such as methoxy-phenol and ethoxy-phenol, nitroso compounds such as p-nitroso-di(phenylhydroxylamine), hydroxylamines, mixtures of metals such as manganese and chelate compounds and so on.

Stabilized Aqueous Solution of Amide

The stabilized aqueous solution of amide of the invention can be stabilized in the co-existence of sulfur containing compound such as thiourea and weak acid salt with an amide. Other additives can co-exist as needed.

Typical examples of a method to make stabilizers co-exist with the amide include a method in which the stabilizers are added to starting materials for producing the amide, a method in which the stabilizers are added in an arbitrary step of the process for producing the amide, a method in which the stabilizers are added to the aqueous solution of amide after the process for producing the amide have finished and so on.

The aqueous solution of amide of the invention comprises an amide, a sulfur-containing compound and a weak acid salt. The amount or concentration of the amide in the aqueous solution is not limited specifically. However, the concentration is preferably in the range of 5 to 80 weight %, and is more preferably in the range of 10 to 60 weight %.

The amount of the sulfur-containing compound in the aqueous solution is preferably in the range of 1 to 100 ppm, and is more preferably in the range of 1 to 30 ppm, based on the weight of the amide respectively.

The amount of the weak acid salt in the aqueous solution is preferably in the range of 1 to 3,000 ppm, and is more preferably in the range of 1 to 2000 ppm, based on the amount of the amide respectively.

If the amount of sulfur-containing compound and the amount of weak acid salt are in the range described above, the effect of stabilizing the aqueous solution of amide during its preservation is sufficient. Furthermore, it is industrially beneficial to use the sulfur-containing compound and the weak acid salt in the range described above. Because these polymerization retarders are less influential in the polymerization reaction, in which an amide having an unsaturated bond is polymerized to produce a corresponding polymer product, than other polymerization retarders such as copper ions.

Other additives can be used in the invention as needed. For example, an alkoxyphenol such as methoxyphenol can be used. The amount of the alkoxyphenol is preferably in the range of 1 to 100 ppm, more preferably is in the range of 20 to 50 ppm, based on the amount of the amide respectively.

Stabilized Crystalline Amide

The crystalline amide of the invention can be stabilized in the co-existence of sulfur-containing compound such as thiourea and weak acid salt with an amide. Other additives can co-exist as needed. The same type of amide, weak acid salt and other additives as described above can be used.

Typical examples of a method to make stabilizers co-exist with the amide include a method in which the stabilizers are added to the starting material for producing the amide, a method in which the stabilizers are added in an arbitrary step of the process for producing the amide and then crystals are formed from the amide, a method in which the sulfur-containing compound and the weak acid salt are directly added to a wet amide crystals which are separated from a slurry in a crystallization step, a method in which thiourea and an weak acid salt are dissolved or dispersed in a medium such as water and sprayed on wet amide crystals and so on.

Water, solvent and so on are removed from the amide crystals in the manner of conventional drying under atmospheric pressure or reduced pressure. Then crystalline amide as a product is obtained. The crystalline amide of the invention comprises a sulfur-containing compound and a weak acid salt.

The amount of the sulfur-containing compound is preferably in the range of 1 to 100 ppm, and is more preferably in the range of 1 to 30 ppm, based on the weight of the amide respectively.

The amount of the weak acid salt is preferably in the range of 1 to 3,000 ppm, and is more preferably in the range of 1 to 2,000 ppm, based on the weight of the amide respectively.

If the amount of sulfur-containing compound and the amount of weak acid salt are in the ranges described above, the effect of stabilizing the amide crystals during its preservation is sufficient, and then the crystals are not likely to coagulate.

Furthermore, it is industrially beneficial to use the sulfur-containing compound and the weak acid salt in the range described above. Because these polymerization retarders are less influential in the polymerization reaction, in which an amide having an unsaturated bond is polymerized to produce a corresponding polymer product, than other polymerization retarders such as copper ions.

Other additives can be used in the amide crystals of the invention as needed. For example, an alkoxyphenol such as methoxyphenol can be used. The amount of the alkoxyphenol is preferably in the range of 1 to 100 ppm, more preferably in the range of 20 to 50 ppm, based on the weight of the amide respectively.

The invention will be illustrated in more detail by way of the following examples, but the invention is not deemed to be limited thereto.

COMPARATIVE EXAMPLES 1 TO 4 AND EXAMPLE 1

Catalyst for Hydration

A Raney copper alloy having a granular size of 80 mesh or less was developed with caustic soda (sodium hydroxide) by conventional method, and then washed to prepare a Raney copper catalyst. During the preparation and in subsequent handling, the contact of the catalyst with a gas containing oxygen such as air was avoided.

Catalytic Hydration Reaction 400 g of the above-mentioned catalyst was placed in a SUS reactor, having a volume of about 2 liters equipped with a stirrer and a catalyst separator therein. Acrylonitrile and water from which dissolved oxygen was previously removed by the use of a nitrogen gas were then fed at flow rates of 600 g/hr and 900 g/hr, respectively, and a reaction was carried out at 120° C. The reaction solution was stirred together with the catalyst to become a suspension, and this suspension was then passed through the catalyst separator and took out from the reactor as a substantially catalyst-free solution. This reaction was continued for 3 days.

Concentration

The obtained reaction solution was concentrated under reduced pressure by a batchwise technique so that the total amount of unreacted acrylonitrile and a part of unreacted water were distilled off, thereby obtaining an aqueous acrylamide solution having a concentration of about 50% by weight. The thus obtained aqueous acrylamide solution contained copper ions and acrylic acid.

In order to conduct a stability test, copper ions and acrylic acid contained in the solution were removed in the manner described below.

Purification

A glass column was filled with 150 ml of a strongly acidic cation exchange resin Lewatit SP-112 (trade name, made by Bayer AG) which was pretreated with dilute hydrochloric acid in accordance with a conventional procedure.

Another glass column was filled with 300 ml of a weakly basic anion exchange resin Lewatit MP-64 (trade name, made by Bayer AG) which was pretreated with aqueous solution of caustic soda in accordance with a conventional procedure.

The aqueous acrylamide solution having a concentration of about 50% by weight described above was then passed through these glass columns, firstly the column filled with the strongly acidic cation exchange resin and secondly the column filled with the weakly basic anion exchange resin, at a flow rate of 900 ml/hr.

In the obtained solution, the copper content was less than 0.01 ppm, and the acrylic acid content was less than 1 ppm.

Thiourea, nitrobenzene, sodium acrylate and/or methoxyphenol were added to the 50% by weight acrylamide aqueous solution thus obtained, so that each solution contains these additives in amounts shown in the table 1. The pH of each solution is adjusted to 7.0 by adding caustic soda and sulfuric acid.

Preservation stability was evaluated by measuring a time period until gelation occurred in each solution. For the measurement, a test piece made of stainless steel was put into 100 ml of each solution, and the solution was kept in a constant temperature bath of 40° C.

The results are shown in Table 1.

TABLE 1

|  | Thiourea (ppm/AAM) | Nitrobenzene (ppm/AAM) | Sodium Acrylate (ppm/AAM) | Methoxyphenol (ppm/AAM) | Preservation stability (days) |
|---|---|---|---|---|---|
| Comparative Example 1 | 0 | 0 | 0 | 20 | 14 |
| Comparative Example 2 | 0 | 0 | 500 | 20 | 29 |
| Comparative Example 3 | 20 | 0 | 0 | 20 | 100 |
| Comparative Example 4 | 0 | 20 | 500 | 20 | 70 |
| Example 1 | 20 | 0 | 500 | 20 | 130 |

According to the present invention, problems of polymerization of an amide in its production process, during its deposition and during its preservation are prevented. The invention provides markedly stable amide containing aqueous solution and crystalline amide.

What is claimed is:

1. An amide composition comprising acrylamide, a sulfur-containing compound which is thiourea or phenothiazine and a weak acid salt.

2. The amide composition of claim 1, wherein the sulfur-containing compound is thiourea.

3. The amide composition of claim 1, wherein the sulfur-containing compound is present in an amount in the range of 1 to 100 ppm based on the weight of the acrylamide.

4. The amide composition of claim 1, wherein the weak acid salt is a salt of an organic acid which has an acid dissociation exponent of 3.5 to 5.5.

5. The amide composition of claim 1, wherein the weak acid salt is present in an amount in the range of 1 to 3,000 ppm based on the weight of the acrylamide.

6. The amide composition of claim 1, wherein the composition comprises a salt of an organic acid having an acid dissociation exponent of 3.5 to 5.5, thiourea in an amount in the range of 1 to 100 ppm based on the weight of the acrylamide, and the salt of the organic acid is present in an amount in the range of 1 to 3000 ppm based on the weight of the acrylamide.

7. The amide composition of claim 1, wherein the acrylamide is in a crystalline state.

8. The amide composition of claim 1, wherein the composition is an aqueous solution.

9. The amide composition of claim 1, wherein the weak acid salt is selected from the group consisting of sodium acrylate and sodium methacrylate.

10. An amide composition comprising methacrylamide, a sulfur-containing compound which is thiourea or phenothiazine and a weak acid salt.

11. The amide composition of claim 10, wherein the sulfur-containing compound is thiourea.

12. The amide composition of claim 10, wherein the sulfur-containing compound is present in an amount in the range of 1 to 100 ppm based on the weight of the methacrylamide.

13. The amide composition of claim 10, wherein the weak acid salt is a salt of an organic acid which has an acid dissociation exponent of 3.5 to 5.5.

14. The amide composition of claim 10, wherein the weak acid salt is present in an amount in the range of 1 to 3,000 ppm based on the weight of the methacrylamide.

15. The amide composition of claim 10, wherein the composition comprises a salt of an organic acid having an acid dissociation exponent of 3.5 to 5.5, thiourea in an amount in the range of 1 to 100 ppm based on the weight of the methacrylamide, and the salt of the organic acid is present in an amount in the range of 1 to 3000 ppm based on the weight of the methacrylamide.

16. The amide composition of claim 10, wherein the methacrylamide is in a crystalline state.

17. The amide composition of claim 10, wherein the composition is an aqueous solution.

18. The amide composition of claim 10, wherein the weak acid salt is selected from the group consisting of sodium acrylate and sodium methacrylate.

* * * * *